(12) United States Patent
Popovic

(10) Patent No.: US 6,464,500 B1
(45) Date of Patent: Oct. 15, 2002

(54) DENTAL IMPLANT AND ABUTMENT SYSTEM

(76) Inventor: Don Dragoljub Popovic, 15585 Skyline Truck Trail, Jamul, CA (US) 91935

(*) Notice: Subject to any disclaimer, the term of this patent is extended or adjusted under 35 U.S.C. 154(b) by 0 days.

(21) Appl. No.: 09/862,777

(22) Filed: May 22, 2001

(51) Int. Cl.[7] .................................................. A61C 8/00
(52) U.S. Cl. ..................................... 433/173; 433/174
(58) Field of Search ............................. 433/172, 173, 433/174, 175, 176; 206/63.5, 339

(56) References Cited

U.S. PATENT DOCUMENTS

| | | | |
|---|---|---|---|
| 5,368,483 A | * 11/1994 | Sutter et al. | 433/173 |
| 6,203,323 B1 | * 3/2001 | Beaty et al. | 433/173 |
| 6,217,332 B1 | * 4/2001 | Kumar | 433/173 |
| 6,280,192 B1 | * 8/2001 | Groll et al. | 433/173 |
| 6,287,117 B1 | * 9/2001 | Niznick | 433/173 |

* cited by examiner

Primary Examiner—Cary E. O'Connor
(74) Attorney, Agent, or Firm—Calif Tervo

(57) ABSTRACT

A dental implant anchor 10 includes an external body surface that can have threads 14 or be non-threaded and a uniquely designed internal portion 40 for engaging screws, abutments, and insertion tools in one step. Internal portion 40 comprises three sections; a top section 42 including a collar 44, a middle section 50 including threads 54, and a bottom section 60 including a surface 62 designed to engage a wrench, such as a hex wrench. Collar 44, which has an O-ring groove 45, holds implant 10 during insertion and stabilizes abutment 100. Extended surface 62 allows insertion tool 300 to screw and unscrew implant 10 with a doctor's hand piece; improves resistance to lateral forces on abutment 100; and provides a surface for cementing abutment 100 to implant 10.

12 Claims, 3 Drawing Sheets

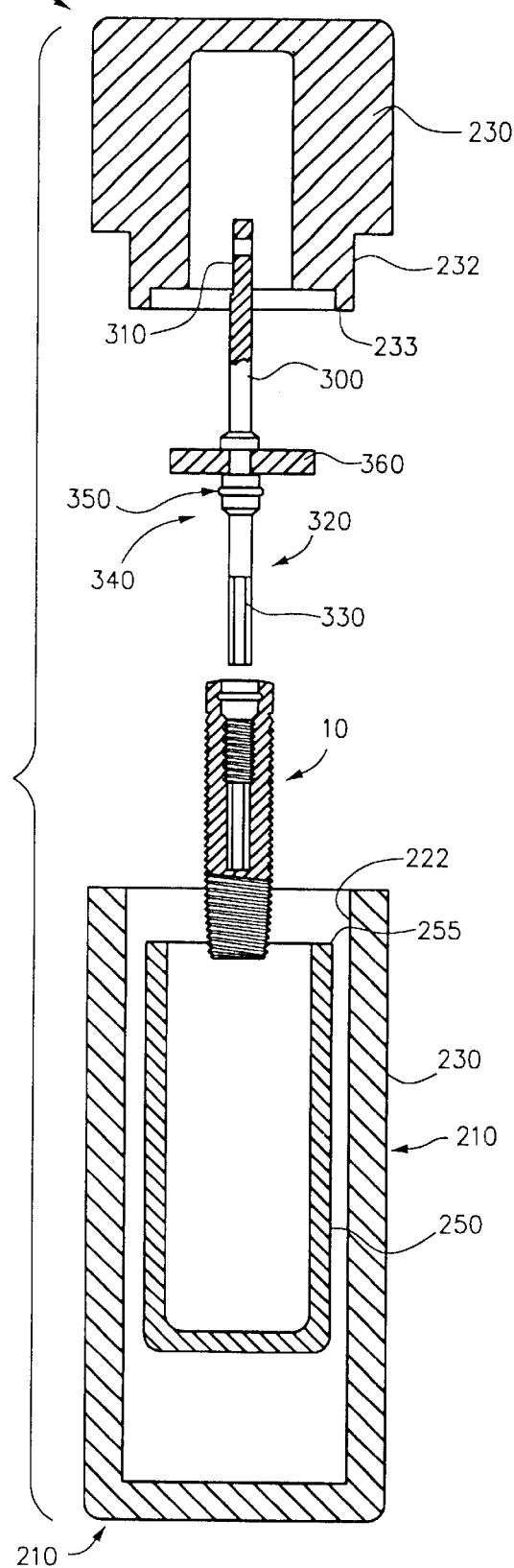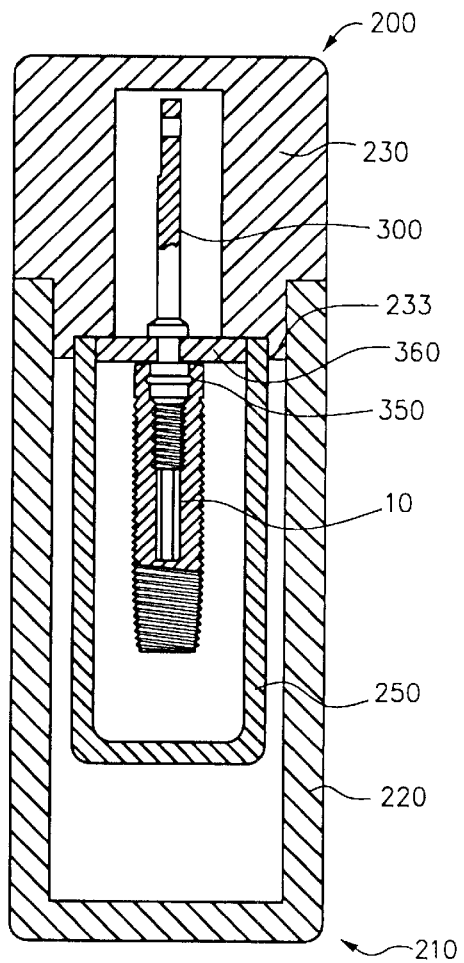
FIG. 3
FIG. 4

DENTAL IMPLANT AND ABUTMENT SYSTEM

FIELD OF THE INVENTION

The present invention is a dental implant system for securing a dental prosthesis to the bone in the mandible or maxilla of a dental patient.

BACKGROUND OF THE INVENTION

Traditional dental implant systems are expensive, mostly because of the number of steps necessary in the implant procedure as well as the number and non-uniformity of parts used to create the dental prosthesis.

In the past, dentists have had to use dental implants that have several different components, each of which increases the chance of introducing non-sterile matter into the patient. Typically, a dental implant consists of the implant, an abutment piece, a screw to anchor the abutment to the implant, and other attachments on the ends of the abutments to fasten the various dental prostheses. Each of these parts adds additional cost in the form of time and materials to both the dentist and the patient.

Another problem with prior dental implants is the non-uniformity of equipment. Each type of dental structure may require a different implant with which to anchor the structure to the jaw of the patient.

It is, therefore, the principal object of the present invention to provide a system and method to implant a dental prosthesis in a patient's mouth that is substantially less expensive, stronger, safer, and consumes less time to implement than the existing art dental implant assemblies.

Another object of the invention is to provide an improved universal abutment that can be connected to various sized implants and can be adapted to attach various dental prostheses. Such an abutment system will provide more stability from lateral, rotational, and axial forces than current dental implant structures and therefore is less likely to become disengaged from the patient.

SUMMARY OF THE INVENTION

This dental implant anchor consists of an external body surface that can be either threaded or non-threaded and a uniquely designed internal structure to engage screws, abutments, and insertion tools in one step. The internal portion consists of three unique sections that have not been used in dental implant technology before. The top consists of a typical collar, the middle consists of the typical threads, and the bottom is a unique design that extends the length of the threaded portion with a surface designed to engage a wrench, such as a hex wrench. The collar, which has an O-ring groove, holds the dental implant during insertion and stabilizes the dental abutment. The collar design increases physical strength because the area between body and threads on the second stage is drastically improved. It also increases stability of the second stage abutment wall-to-wall connection. The middle threaded section fixes the abutment and screws. The unique bottom extended surface offers three important functions not previously used in the technology: 1) It allows the insertion tool to screw and unscrew the dental implant with the doctor's hand piece; 2) It improves resistance to lateral forces on the abutment; and 3) It provides a surface to cement the abutment to the dental implant anchor.

A novel system for packaging and insertion of this implant has been developed to allow for sterile shipment and installation of the implant. The packaging comprises an external capsule structure with a lower outer cover tube and an upper outer cover tube. The diameter of the interface region on the upper outer cover tube is slightly smaller than that of the lower outer cover tube in the corresponding region to allow the end of the upper tube to slide inside the lower outer cover tube. The outer capsule (lower and upper tubes) is removed, and there is a lower internal tube that covers the implant that is attached to the insertion tool, leaving the upper end of the insertion tool free to be attached to the dentist's hand piece. After the upper end of the insertion tool is attached to the hand piece, the lower internal tube is removed and the implant is ready for insertion. The lower internal tube has a diameter slightly smaller than that of the upper outer cover tube to allow the end of the lower internal tube to be inserted in the end of the upper outer cover tube, securing it in place. The insertion tool has a wrench on one end that fits in the wrench engaging surface of the implant or abutment; the other end is adapted for use in a dentist's hand piece; and a collar in the middle separates the two regions. The insertion tool has an O-ring in the area above the wrench end that holds the implant to the insertion tool during shipment and insertion. The insertion tool has another O-ring above the collar that holds the insertion tool and implant to the lower internal tube of the packaging.

In summary, this dental implant system has the following novel features:

1) Uniform internal dimensions to allow use of a universal abutment for all types of dental prostheses.
2) A wrench that engages in the area beneath the internal threaded surface to allow easy implantation and extraction of the implant.
3) Overall increased internal length to allow for increased stability and resistance to lateral forces with the use of the described abutment device.
4) The wrench engaging area provides an area in which dental cement may be applied to further affix the abutment and provide increased stability, decreasing the possibility that the prosthesis or abutment will become disengaged from the implant.
5) An upper region allows for improved force dissipation and acts to secure the implant to the implantation tool during insertion.
6) A single piece abutment system allows the same abutment to be used for all sizes of dental implants and can be used with a variety of dental prostheses as a way to make this implant system more cost effective for dentists and patients.

These and other advantages will become apparent from the following description of the preferred embodiment in conjunction with illustrative figures, although variations and modifications may be effected without departing from the spirit and scope of the novel concepts of the disclosure.

BRIEF DESCRIPTION OF THE DRAWINGS

FIG. 3 is a exploded side elevation view, partially in cross section, of packaging including the implant and an insertion tool.

FIG. 4 is a side elevation view, partially in cross section, of the assembled packaging of FIG. 3.

DETAILED DESCRIPTION OF A PREFERRED EMBODIMENT OF THE INVENTION

The invention disclosed herein is a dental implant system to secure dental prostheses into the underlying bone in the mandible or maxilla of a dental patient.

Figure 1:
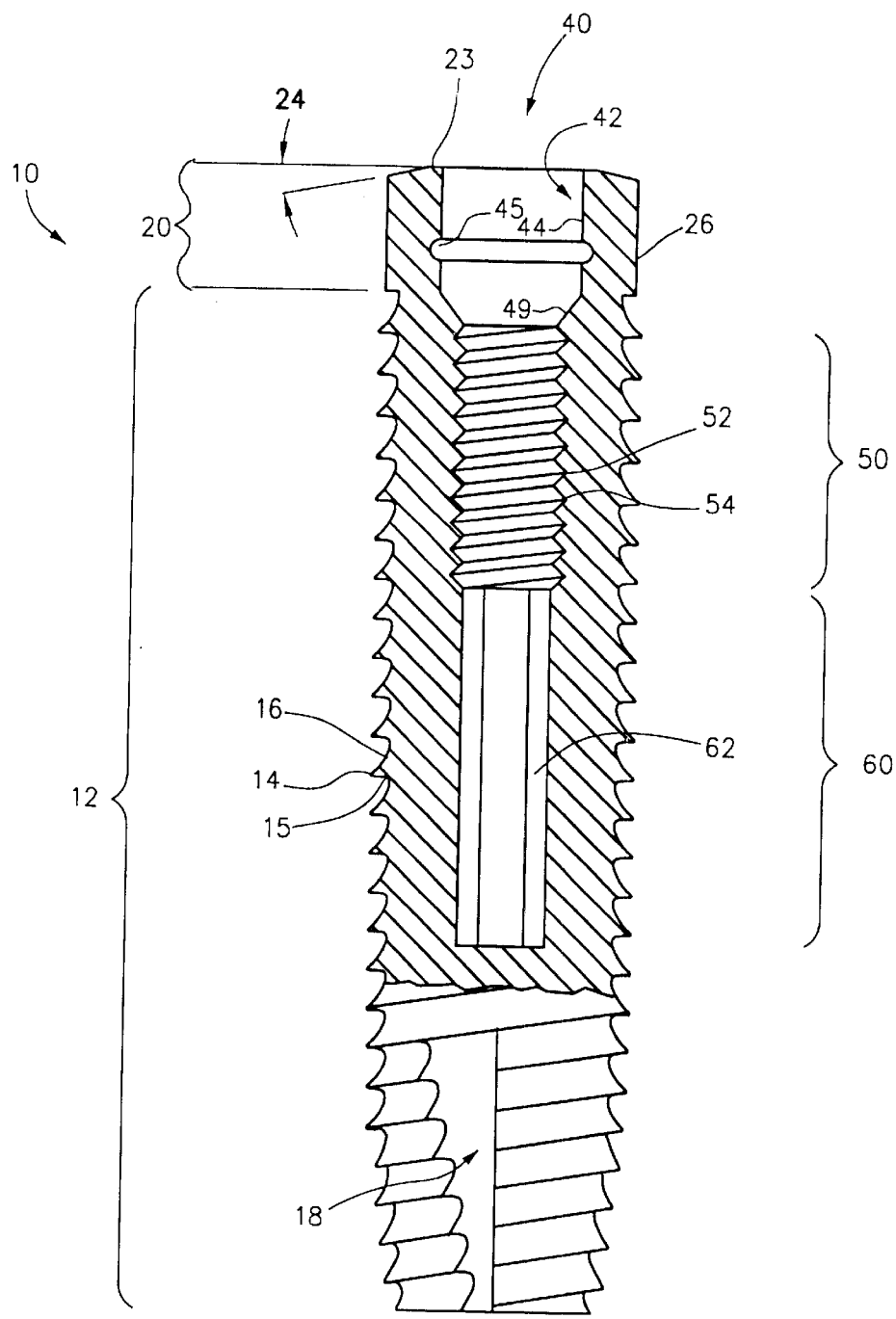
FIG. 1 is a side elevation view, partially in cross section, of a dental implant according to the invention.
Figure 2:
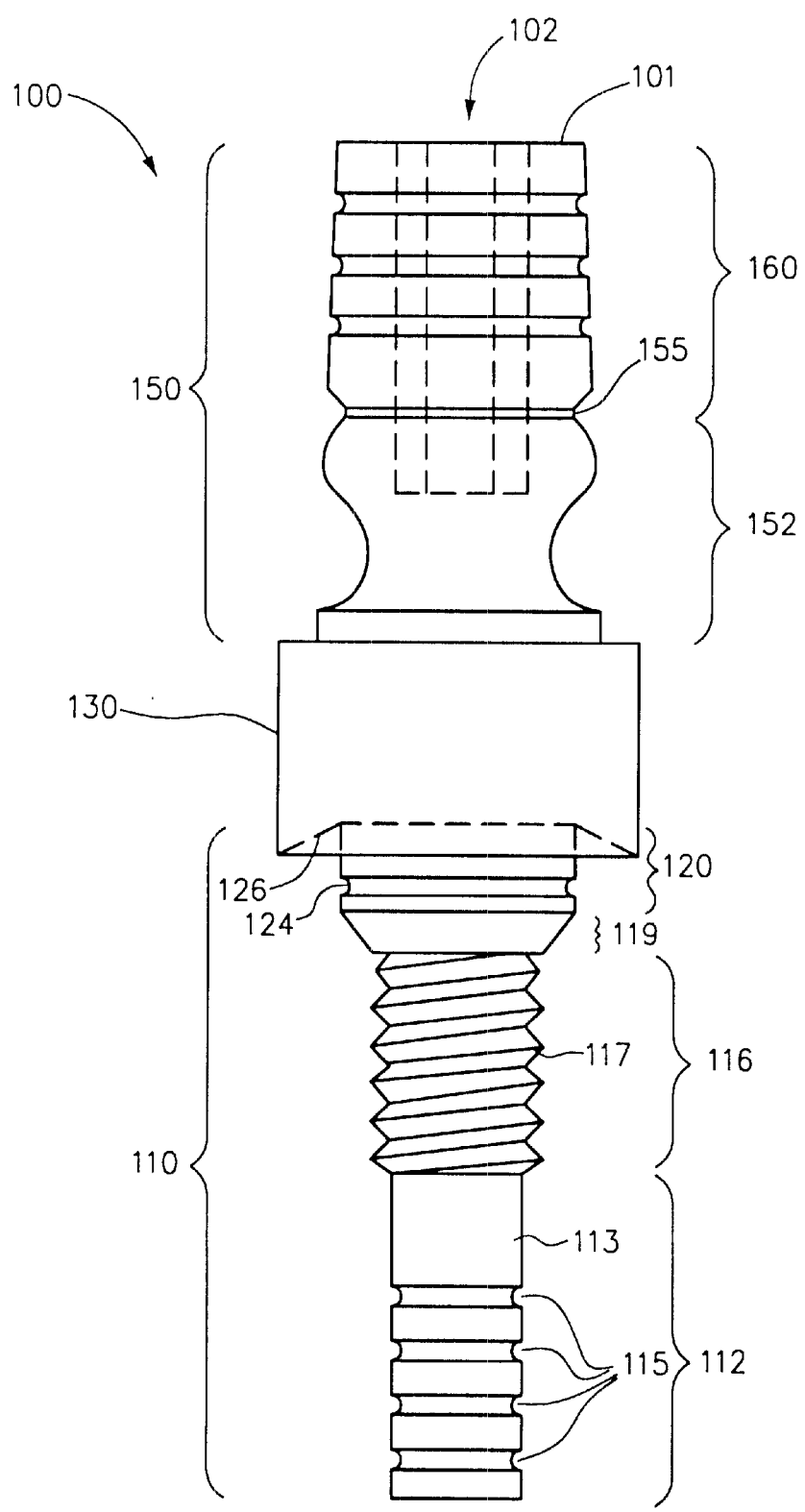
FIG. 2 is a side elevation view of an abutment.

FIG. 1 is a side elevation view, partially in cross section, of a dental implant 10 according to the invention. FIG. 2 is a side elevation view of an abutment 100.

The invention consists of a dental implant piece, such as implant 10, and an abutment 100. The two pieces, 10, 100, connect through a threaded interface with the threads 54, 117 lining a portion of the internal surface of the implant 10 and the external surface of the abutment, respectively.

The implant 10 is a single piece made of a bio-compatible material, such as titanium, comprising the following regions: a root region 12 that is implanted in the bone, and a coronal region 20 that extends from the jaw bone and allows for attachment of an abutment 100. Coronal region 20 includes a front angle 24 that helps lock the abutment 100 and cover screw (not shown) and prevent their lateral movement. A flat, non-threaded concave area 26 seals areas in the bone around the upper section of implant 10. The diameter of area 26 varies with size of implant 10. Root region 12 includes external threads 14. In best mode, threads 14 have a bottom surface 15 flatter than upper surface 16 so as to better dissipate radial forces. Threads 14 have a concave upper surface 15. Three axial grooves 18 allow for better osseointegration, increased resistance to rotational force, and an edge for increased bone cutting.

A An internal portion 40 consists of three unique sections that have not been used in dental implant technology before. The top section 42 consists of a typical internal collar 44, the middle section 50 consists of the typical threaded portion 52 including threads 54, such as 2/56 threads having a length of 0.120 inch, and the bottom section 60 is a unique design that extends the length of the threaded portion 52 with a surface 62, such as an extended hex surface, designed to engage a wrench, such as a hex wrench. Internal collar 44 diameter is typically 0.125 inch. Threaded portion 52 is adapted for securing abutment 100 or screws. The collar 44, which has an O-ring groove 45, holds dental implant 10 to the insertion tool 300 during insertion and stabilizes the dental abutment 100. The design of internal collar 44 increases physical strength because the area between body and threads on the second stage is drastically improved. It also increases stability of the second stage abutment wall-to-wall connection. A transition area 49 is located between collar 44 and threads 54. The middle threaded section 50 fixes the abutment and screws. Overall length of implant 10 is 0.400 to 0.714 inches, depending upon implant size.

Abutment 100 provides the attachment means for the dental prosthesis. Abutment 100 comprises three main regions: a lower root region 110 adapted for insertion into implant 10, an upper coronal region 150 adapted for attachment of various dental prostheses, and an external collar 130 therebetween. Abutment 100 has a wrench engaging bore 102 extending axially from the apex 101 of abutment 100 to the top of the external collar 130. There is also a groove 155 cut circumferentially around the coronal region 150 between the external collar 130 and the apex 101 of the coronal region 150 that allows abutment 100 to be cut at this level and thus adapted for use in various types of dental prostheses.

Root region 110 includes, starting from lower end, extended region 112, threaded region 116, connection region 119, and stabilizing region 120. Extended region 112 is adapted for insertion into the wrench engaging surface 62 in dental implant 10 and provides lateral stabilization and a surface for application of dental cement to secure abutment 100 to implant 10. Grooves 115 in extended region 112 allow a better surface for cementation of abutment 100 to dental implant 10. Threaded region 116 is for insertion into internal bore 40 of implant 10 for attachment to threaded portion 54. Connection region 119 transitions between threaded region 116 and stabilizing region 120. Stabilizing region 120 is adapted to fit internal collar 44 of implant 10. Stabilizing region 120 includes a groove 124 for an O-ring to seal and protect the internal collar 44 of implant 10. A groove 124 in stabilization region 120 for the O-ring, rubber seal, and cementation seals, to allow cement and O-ring to lock into place. Locking region 126 is adapted to lock onto front angle 24 on top 23 of implant 10.

Coronal region 150 includes a lower attachment region 152 and a upper attachment region 160. Lower attachment region 152 is adapted to fit a dental prosthesis. Groove 155 between lower attachment region 152 and upper attachment region 160 allows abutment 100 to be adapted to different dental prostheses by cutting at this groove 155. If upper attachment region 160 has been removed by cutting at groove 155, there is a wrench engaging surface 102 that extends axially into lower attachment region 152 allowing the dentist to install abutment 100 into implant 10. Attachment region 150 is adapted to fit a dental prosthesis. Wrench engaging surface 102 is bored axially into upper attachment region 160 and extended below groove 155 between regions 160 and 152 allowing the dentist to install abutment 100 in implant 10.

FIG. 3 is a exploded side elevation view, partially in cross section of packaging 200 including the implant 10 and an insertion tool 300. FIG. 4 is a side elevation view, partially in cross section, of the assembled packaging 200 of FIG. 3.

The packaging 200 comprises an external capsule structure 210 with a lower outer cover tube 220 and an upper outer cover tube 230. Lower outer cover tube 220 attaches to upper outer cover tube 230. The diameter of the interface region 232 on the upper outer cover tube 230 is slightly smaller than that of interface region 222 of the lower outer cover tube 220 in the corresponding region to allow the end 233 of the upper outer cover tube 230 to slide inside the lower outer cover tube 222.

Upper outer cover tube 230 encloses insertion tool 300 and connects to both lower outer cover tube 222 and internal cover tube 250. The outer capsule 210 (lower and upper tubes 220, 230) is removed, and there is an lower internal tube 250 that covers the implant 10 that is attached to the insertion tool 300 and leaves the upper end 310 of the insertion tool 300 free to be attached to a dentist's hand piece. After the upper end 310 of the insertion tool 300 is attached to the hand piece, the lower internal tube 250 is removed and the implant 10 is ready for insertion. Internal cover tube 250 encloses implant 10 and attaches to upper cover tube 230. The lower internal tube 250 has a diameter slightly smaller than that of the upper outer cover tube 230 allowing the end 255 of the lower internal tube 250 to be inserted in the end 233 of the upper outer cover tube 230, thus securing it in place. The insertion tool 300 has a wrench 330 on lower end 320 that fits in the wrench engaging surface 62 of the implant 10 or abutment 100. The upper end 310 is adapted for use in a dentist's hand piece. A collar 340 in the middle separates the two regions 310, 320. The insertion tool 300 has an O-ring 350 in the area above the wrench end 330 that holds the implant 100 to the insertion tool 300 during shipment and insertion. The insertion tool 300 has another O-ring 360 above the collar 340 that holds the insertion tool 300 and implant 10 to the lower internal tube 250 of the packaging 200.

I claim:

1. A dental implant for attachment of an abutment to the bone of a dental patient; the abutment having a stabilizing region and a threaded region; said implant including:

an internal bore including:
  a lower region that is adapted as a wrench engaging surface;
  a middle region including threads adapted for attachment of the threaded region of the abutment; and
  an upper collar region adapted for receiving the stabilizing region of the abutment.

2. The dental implant of claim 1 wherein:
said implant is generally cylindrical in shape.

3. The dental implant of claim 2 further including:
an exterior root region including:
  an exterior threaded surface.

4. The dental implant of claim 3 wherein:
said exterior threaded surface includes:
  a plurality of axial grooves cut along the outer surface providing a bone cutting edge.

5. A dental implant system comprising:
a dental implant for attachment to the bone of a dental patient including:
  an internal bore including:
    a lower region that is adapted as a wrench engaging surface;
    a middle region including:
      threads; and
    an upper collar region including
      a collar; and
  an abutment for attachment to said dental implant including:
    a root region including:
      a threaded region adapted for attachment to said threads of said middle region of said implant; and
      a stabilizing region adapted to fit in said collar of said collar region.

6. The dental implant system of claim 5 wherein:
said implant is generally cylindrical in shape.

7. The dental implant system of claim 6 wherein:
said implant further includes:
  a root region including:
    an exterior threaded surface for attachment to a bone of a dental patient.

8. The dental implant system of claim 7 wherein:
said exterior threaded surface includes:
  a plurality of axial grooves cut along the outer surface providing a bone cutting edge.

9. The dental implant system of claim 5 wherein:
said root region of said abutment further includes:
  an extended region below said threaded region adapted to fit into said lower wrench engaging surface of said dental implant.

10. The dental implant system of claim 9 wherein:
said extended region of said abutment is cylindrical in shape.

11. The dental implant system of claim 9 wherein:
said abutment further includes:
  an upper coronal region connected to said root region and adapted for attachment of various dental prostheses; said coronal region having an upper apex and including:
    a circumferential groove for facilitating cutting off of said abutment at said groove for adapting said coronal region for use with different dental prostheses; and
    an internal wrench engaging bore extending from the apex of said abutment to below said groove.

12. The dental implant system of claim 5 wherein:
said abutment further includes:
  an upper coronal region connected to said root region and adapted for attachment of various dental prostheses; said coronal region having an upper apex and including:
    a circumferential groove for facilitating cutting off of said abutment at said groove for adapting said coronal region for use with different dental prostheses; and
    an internal wrench engaging bore extending from the apex of said abutment to below said groove.

* * * * *